US00PP25641P3

(12) United States Plant Patent
Li

(10) Patent No.: US PP25,641 P3
(45) Date of Patent: Jun. 23, 2015

(54) *VERBENA* PLANT NAMED 'KLEVP13455'

(50) Latin Name: ***Verbena* sp.**
Varietal Denomination: KLEVP13455

(71) Applicant: Klemm+Sohn GmbH & Co. KG, Stuttgart (DE)

(72) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 78 days.

(21) Appl. No.: 13/998,503

(22) Filed: Nov. 6, 2013

(65) Prior Publication Data

US 2015/0128322 P1 May 7, 2015

(51) Int. Cl.
*A01H 5/02* (2006.01)

(52) U.S. Cl.
USPC ..... Plt./308

(58) Field of Classification Search
USPC ..... Plt./308
CPC ..... A01H 5/02; A01H 5/00
See application file for complete search history.

*Primary Examiner* — Kent L Bell

(74) *Attorney, Agent, or Firm* — Barbara Campbell; Cochran Freund & Young LLC

(57) ABSTRACT

A new *Verbena* plant particularly distinguished by large pink and white flowers, a semi-trailing plant habit, a high number of branches and medium vigor is disclosed.

1 Drawing Sheet

Genus and species: *Verbena* sp.
Variety denomination: 'KLEVP13455'.

BACKGROUND OF THE NEW PLANT

The present invention comprises a new and distinct variety of *Verbena,* botanically known as *Verbena* sp., and hereinafter referred to by the variety name 'KLEVP13455'. 'KLEVP13455' originated from a controlled cross-pollination conducted in June 2011 in Sydney, Australia between the proprietary female *Verbena* variety 'VC 09 0179' (unpatented), having dark purple flowers with eyes and the proprietary male *Verbena* variety 'VC 10 0152' (unpatented) having pink flowers with eyes.

The seeds from the cross were sown and plants were grown in a greenhouse for evaluation, where an individual plant designated 'KLEVP13455' was selected from the group of plants in October 2011.

In January 2012, 'KLEVP13455' was first vegetatively propagated by vegetative cuttings. 'KLEVP13455' was found to reproduce true to type in successive generations of asexual propagation via vegetative cuttings.

'KLEVP13455' has not been made publicly available or sold more than one year prior to the filing date of this application.

SUMMARY

The following are the most outstanding and distinguishing characteristics of this new variety when grown under normal horticultural practices in Stuttgart, Germany.

1. Large pink and white flowers;
2. A semi-trailing plant habit; and
3. High number of branches and medium vigor.

DESCRIPTION OF THE PHOTOGRAPH

This new *Verbena* plant is illustrated by the accompanying photograph which shows the plant's overall plant habit including form, foliage, and flowers. The photograph is of a 3 to 4-month-old plant grown in a greenhouse in Stuttgart, Germany in May 2013. The colors shown are as true as can be reasonably obtained by conventional photographic procedures.

DESCRIPTION OF THE NEW VARIETY

The following detailed descriptions set forth the distinctive characteristics of 'KLEVP13455'. The data which define these characteristics were collected from asexual reproductions carried out in Stuttgart, Germany and Latina, Italy. Data was collected on 20-week-old plants grown in a greenhouse in Stuttgart, Germany and Latina, Italy in Spring 2013. Color references are to The R.H.S. Colour Chart of The Royal Horticultural Society of London (R.H.S.), 5$^{th}$ edition (2007).

Plant:
- *Growth and branching habit.*—Semi-trailing.
- *Height (from top of soil).*—20.0 cm.
- *Width (horizontal plant diameter).*—40.0 cm.
- *Time to produce a finished flowering plant.*—About 12 weeks from un-rooted cutting.
- *Time to initiate and develop roots.*—2 weeks.
- *Root description.*—Moderate.

Stems:
- *Number of branches per plant.*—Greater than 30.
- *Growth habit.*—Semi-trailing.
- *Length.*—About 20.0 cm.
- *Diameter.*—About 0.2 cm.
- *Internode length.*—About 0.5 cm.
- *Color.*—RHS 139C.
- *Anthocyanin.*—Absent.
- *Texture and appearance.*—Satiny, moderate, pubescence.

Leaves:
- *Arrangement.*—Opposite.
- *Immature and mature leaf color.*—Upper surface: RHS 141B. Lower surface: RHS 139C.

*Length.*—3.0 cm.
*Width.*—1.0 cm.
*Shape.*—Lanceolate.
*Apex.*—Acuminate.
*Base.*—Attenuate.
*Margin.*—Serrate.
*Texture.*—Upper surface: Leathery. Lower surface: Rough.
*Venation type.*—Palmate.
*Venation color* (*both upper and lower surfaces*).—RHS 139D.
*Petioles.*—Length: Less than 0.1 cm. Diameter: Less than 0.2 cm. Color: RHS 139D. Texture: Rough.

Flower buds:
*Shape.*—Cylindrical.
*Length.*—About 1.0 cm.
*Diameter.*—About 0.1 cm.
*Color* (*at tight bud*).—RHS 139D.

Inflorescence:
*Blooming habit* (*flowering season*).—Continuous.
*Lastingness of individual blooms on the plant.*—About 2 weeks.
*Fragrance.*—Absent.
*Inflorescence type.*—Umbel.
*Length of inflorescence.*—4.0 cm.
*Diameter of inflorescence.*—6.0 cm.
*Number of florets per inflorescence.*—About 30.
*Peduncle.*—Color: RHS 139D. Length: 2.0 cm. Diameter: 0.1 cm.

Florets:
*Length.*—1.0 cm.
*Diameter.*—1.5 cm.
*Texture.*—Glossy.
*Form.*—Single.
*Corolla tube length.*—1.0 cm.
*Corolla tube color.*—RHS 139C.
*Petals.*—Color: Immature: Upper surface: RHS 57A and RHS N999D and RHS 57D. Lower surface: RHS N155A. Mature: Upper surface: RHS 57C and RHS N999D and RHS 57C. Lower surface: RHS N155A. Length of lobe: 1.0 cm. Diameter of lobe: 0.7 cm. Lobe shape: Reniform. Apex: Obtuse. Base: Fused. Margin: Crenate. Texture: Upper surface: Shiny. Lower surface: Glossy.
*Pedicels.*—Length: 1.0 cm. Diameter: 0.1 cm. Color: RHS N155A. Texture and appearance: Glossy. Arrangement: Composed of more than 20 sepals arranged in a single row.

Sepals:
*Shape.*—Lanceolate.
*Apex.*—Cuspidate.
*Base.*—Fused, closed.
*Margin.*—Entire.
*Length.*—1.0 cm.
*Diameter.*—0.1 cm.
*Color.*—RHS 139C.
*Texture* (*both upper and lower surfaces*).—Hairy (pubescent).

Reproductive organs:
*Stamens.*—Present. Quantity: 5. Appearance: Long. Color: RHS 139C. Filament length: 0.2 cm. Filament diameter: Less than 0.1 cm. Anther: Shape: Long. Color: RHS N999D. Length: Less than 0.1 cm. Diameter: Less than 0.1 cm. Pollen amount: Sparse.
*Pistils.*—Number: 1. Length: 0.5 cm. Diameter: Less than 0.1 cm. Stigma: Color: RHS N999D. Appearance: Filamentous. Length: Less than 0.4 cm. Diameter: Less than 0.1 cm. Style: Color: RHS N999D. Length: Less than 0.4 cm. Diameter: Less than 0.1 cm. Appearance: Round.

Fruit and seed set: Present; seeds are long and acuminate.
Disease and pest/insect resistance: Resistant to mildew.

COMPARISON WITH PARENTAL LINES AND KNOWN VARIETY

'KLEVP13455' is a distinct variety of *Verbena* having pink and white flowers. 'KLEVP13455' is distinguished from its parents, as described in Table 1.

TABLE 1

Comparison with Parental Lines

| Trait | Variety 'KLEVP13455' | Female parent 'VC 09 0179' | Male Parent 'VC 10 0152' |
|---|---|---|---|
| Flower color | Pink and white | Dark purple with eye | Pink with eye |
| Habit | Semi-trailing | Mounding | Mounding |
| Flower size | Big | Big | Big |

'KLEVP13455' is most similar to the commercial *Verbena* variety LANAI 'Twister Pink' (patent status unknown). Differences between the varieties are described in Table 2.

TABLE 2

Comparison with Similar Variety

| Trait | Variety 'KLEVP13455' | Commercial line LANAI 'Twister Pink' |
|---|---|---|
| Habit | Semi-trailing | Trailing |
| Vigor | Medium | Strong |
| Branching | High | Low |

I claim:

1. A new and distinct variety of *Verbena* plant designated 'KLEVP13455' as illustrated and described herein.

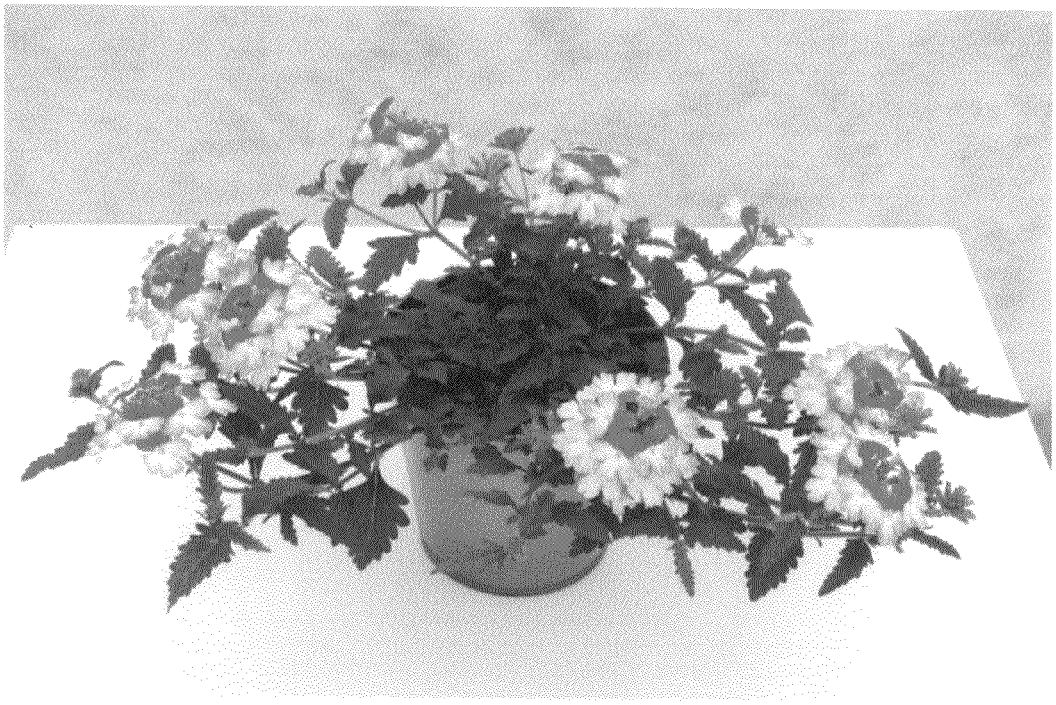

* * * * *